United States Patent [19]

Westernacher et al.

[11] 4,388,216

[45] Jun. 14, 1983

[54] REGENERATING HEAVY METAL CATALYSTS FOR BUTYNEDIOL PRODUCTION

[75] Inventors: Helmut Westernacher, Haltern, Fed. Rep. of Germany; Franz Schämann, deceased, late of Marl, Fed. Rep. of Germany, by Elfriede Schämann, Ilka Schämann, heirs

[73] Assignee: GAF Hüls Chemie GmbH, Marl, Fed. Rep. of Germany

[21] Appl. No.: 171,000

[22] Filed: Jul. 21, 1980

[30] Foreign Application Priority Data

Jul. 21, 1979 [DE] Fed. Rep. of Germany ....... 2929586

[51] Int. Cl.$^3$ ............ B01J 31/40; B01J 23/94; C07C 33/046; C07C 29/00
[52] U.S. Cl. .................................. 252/412; 252/416; 568/855
[58] Field of Search ............... 252/416, 419, 420, 413; 568/855

[56] References Cited

U.S. PATENT DOCUMENTS

| 3,920,759 | 11/1975 | Hort | 568/855 |
| 4,119,790 | 10/1978 | Hort | 568/855 |

FOREIGN PATENT DOCUMENTS

| 134840 | 3/1979 | German Democratic Rep. | 252/420 |
| 2206693 | 8/1973 | Fed. Rep. of Germany | 568/855 |
| 134840 | 3/1979 | Fed. Rep. of Germany | 252/420 |
| 274094 | 6/1970 | U.S.S.R. | 252/415 |

*Primary Examiner*—P. E. Konopka
*Attorney, Agent, or Firm*—Wells & Wells

[57] ABSTRACT

A process for regenerating suspended heavy metal catalysts used in the synthesis of butynediol from acetylene and formaldehyde. The aqueous catalytic slurry removed from the reaction mixture is raised to a temperature of about 200° to 500° C., where appropriate with air supplied, and is left at this temperature with air being supplied, until the carbon content of the catalytic substance is about 0.5 to 3%.

6 Claims, No Drawings

REGENERATING HEAVY METAL CATALYSTS FOR BUTYNEDIOL PRODUCTION

CROSS REFERENCE TO RELATED APPLICATION

Applicants claim priority under 35 USC 119 for application P 29 29 586.1, filed July 21, 1979 in the Patent Office of the Federal Republic of Germany.

BACKGROUND OF THE INVENTION

The field of the invention is acetylenically unsaturated, polyhydroxy, acyclic, organic compounds and the invention is particularly concerned with the regeneration of copper catalysts used in suspended form for the production of butynediol from acetylene and formaldehyde.

The state of the art of butynediol (2-butyne-1,4-diol) production and the catalysts used therein may be ascertained by reference to the Kirk-Othmer, "Encyclopedia of Chemical Technology", 2nd Edition, Vol. 1 (1963) pp. 502–611; U.S. Pat. Nos. 3,920,759; 3,954,669; 4,067,914; 4,119,790; and 4,127,734; and West German Published Applications 2,206,693 and 2,602,418, the disclosures of which are incorporated herein.

Besides the main component copper, used in the butynediol production, the catalysts also may contain other metals such as chromium, silver, bismuth and cobalt. As a rule, a copper/bismuth catalyst is used. For safety reasons, and in view of reaction engineering requirements, the catalysts are used in the form of carrier catalysts. Appropriate carrier materials are silicates and oxides such as magnesium silicate, pumice, silica gel, kieselguhr, silicon dioxide, magnesium dioxide, barium oxide, calcium oxide and aluminum oxide. For practical considerations, silicates and aluminum oxide are preferred.

The conversion of the catalysts into the catalytically active form can be carried out as described in West German Published Application 26 02 418 and U.S. Pat. Nos. 4,067,914; 3,920,759 and 3,954,669.

These catalysts suspended in the reaction medium for the production of butynediol lose their activity with time, and furthermore their separation from the reaction mixture becomes more difficult as the catalysts age. When filters are employed a significant drop in filtering capability is observed.

This loss in activity of the catalysts is attributed essentially to a deposition of carbon compounds on the active centers, for instance the formation of cuprene during the reaction. It is therefore necessary to remove in a continuous or a discontinuous manner, the used catalyst from the reactors and to replace the used catalyst with a fresh one.

U.S. Pat. No. 4,119,790 discloses a continuous, multi-stage, low pressure ethynylation process for the production of butynediol. The steps of the process include:

(a) continuously reacting formaldehyde and acetylene in a first stage reaction zone at a partial pressure of acetylene of less than 2 atmospheres and a reaction temperature of about 80° to about 105° C., in a stirred aqueous medium, in the presence of an ethynylation catalyst slurry consisting essentially of a finely divided water-insoluble complex cuprous acetylide powder made from a catalyst precursor material containing greater than 20% and less than 35% by weight of copper, 0 to about 3%, and preferably 2–3% by weight of bismuth on a magnesium silicate carrier therefor, to form a first stage reaction product containing butynediol;

(b) continuously withdrawing the first stage reaction product and the catalyst slurry as a first stage effluent;

(c) continuously passing the first stage effluent into a second stage reaction zone into which additional acetylene is being supplied;

(d) repeating steps (b) and (c), if desired, to other additional stage reaction zones to produce a final stage effluent;

(e) continuously withdrawing the final stage effluent;

(f) continuously separating the final stage effluent by adding into catalyst-free liquid containing the butynediol and a concentrated catalyst slurry; and (g) continuously recycling the concentrated catalyst slurry to the first reaction zone.

The regeneration of old catalyst is generally known. West German Published Application 22 06 693 emphasizes the simple regeneration of the suspended catalyst with respect to the formed catalyst as mounted in a solid bed (Column 2, lines 34 through 41) specifically for the production of butynediol in the presence of copper carrier catalysts.

A specific proportion of the catalyst suspended in the reaction medium is continuously removed by a sludge centrifuge and washed several times with water and regenerated by dissolving the metals in nitric acid and by the ensuing step of precipitation, and then the regenerated catalyst is fed in the form of a pumpable suspension back into the reactor (Column 4, last paragraph).

On the one hand this process is relatively costly in view of the many steps required, and on the other hand the application of nitric acid places high requirements on the materials of the regeneration apparatus. This process further suffers from the drawback that operating with nitric acid may cause health problems.

SUMMARY OF THE INVENTION

Having in mind the limitations of the prior art, it is an object of the present invention to satisfactorily restore the nature and activity of suspension catalysts used in the manufacture of butynediol.

This object is satisfactorily achieved in a surprisingly simple manner according to the present invention, wherein an aqueous catalyst slurry is removed from the reaction mixture and raised to a temperature of about 200° to 500° C., preferably 250° to 350° C., with air being supplied, and is left at this temperature with the air being supplied until the carbon content of the catalytic substance is about 0.5 to 3%. Carbon contents less than about 1% are preferred.

DESCRIPTION OF THE PREFERRED EMBODIMENTS

It must be kept in mind regarding the lower carbon content that values approaching 0% should be sought, but commercially this is costly on account of the long duration of the thermal treatment and the possible undesired effects associated therewith.

The catalyst treatment of the present invention may be carried out at low economic cost and entails no damage to the carrier grain, and furthermore, the original activity is practically entirely restorable.

The process of the present invention is implemented as follows: the catalytic sludge removed by filtration or centrifuging from the reaction mixture and generally containing from about 20 to 70% water is put into an apparatus that can be electrically or steam heated. Preferably the heating is carried out externally.

The container holding the catalyst to be regenerated is equipped with means for temperature and pressure metering. It is furthermore provided with an air hookup and most often also a filter-equipped discharge to the atmosphere.

The catalyst substance may be stirred in the container during the heat treatment. The temperature advantageously is kept within the desired limits by revolving the catalytic material, and thereby local overheating is eliminated. If the catalytic material is at rest, it is recommended that the air be supplied alternatingly to various locations.

Oxygen containing gases may also be used in lieu of air, but air is preferred because it is the most economical source of oxygen containing gases.

When heating proceeds for some time during the evaporation of the main portion of the water, then exothermal self decomposition takes place in the catalytic material, whereby the defined temperature ranges from about 200° to 500° C. is sustained without an external supply of heat. The sudden onset of the exothermal self-decomposition depends on the water content of the catalytic sludge and on the proportion of cuprous acetylide in the sludge.

It is essential for the process of the invention that the limits of the defined temperature range be observed, as there is a danger at temperatures about 500° C. that the catalyst will be destroyed and at temperatures below 200° C. that the combustion of the carbon ingredients will not be ensured.

The termination of the regeneration process can be observed optically in that a fine-particulate, uniformly gray powder has been obtained from the red-brown old catalytic substance, the appearance of this powder corresponding to the fresh catalyst.

The process may be visually monitored through a viewing window in the apparatus.

In the process of the present invention, the termination of the regeneration is ascertained by a carbon determination. The process is completed when the carbon content is between about 0.5 and 3%, preferably less than 1%.

The determination of the carbon content is ascertained by combustion at about 900° to 1000° C., with poor oxygen, until carbon dioxide is obtained, the latter being determined by quantitative analysis.

The catalyst regenerated by the process of the present invention is suitably added directly into the ethynylation process in making butynediol from acetylene and formaldehyde.

The process of the present invention is described below in further detail with relation to specific examples.

EXAMPLE 1

500 kg of old catalyst with clearly reduced activity are removed from a commercial butynediol production facility as disclosed in U.S. Pat. No. 4,119,790 and filled into a 750 liter container for the purpose of regeneration.

The features of the old catalytic sludge are as follows:

| | |
|---|---|
| water content | 45% by weight |
| carrier material | magnesium silicate |
| copper content in solid | 25.1% |
| bismuth content in solid | 2.5% |
| carbon content in solid | 9.9% |
| grain size distribution | <10 microns = 23% |
| | <24 microns = 99.4% |
| | >90 microns = 0.3%. |

This substance is heated externally for about 8 hours at 2 bars of steam without being revolved. Thereupon the external heating is shut off because the heat generated by the decomposition of the catalyst is sufficient to sustain the reaction and to evaporate the residual water.

The substance is turned over for another 24 hours by rotating the container and a supply of air ensures the continuation of the reaction of decomposition and the oxidation of the heavy metals without there being a drop in temperature. The temperature did not exceed 300° C. Upon completion of the regeneration, 300 kg of catalyst in the form of a gray powder is obtained, which in its characteristics and in its activity is equivalent to a fresh catalyst. The carbon determination showed a 0.9% carbon content.

Characteristics of the regenerated catalyst:

| | |
|---|---|
| copper content | 25.3% by weight |
| bismuth content | 2.9% by weight |
| grain size distribution | <10 microns = 26.0% |
| | <45 microns = 99.8% |
| | >90 microns = 0.1%. |

The conversion of the regenerated catalyst into the active state is carried out as follows:

100 g of catalyst are introduced into 2000 g of a 30% formaldehyde solution. 15 ml of glacial acetic acid are added to the dispersion. Acetylene is fed into the reactor with stirring at 93° C. and a pressure of 0.5 bars until the formaldehyde content in the reaction mixture drops to below 2% (about 35 hours). The exhaust flow is set to 40 to 50 ml/min. Upon completion of the reaction, the activated catalyst was removed from the reactor and washed with water until product-free. In that form it is then used in the activity test. The catalysts are interstratified under water. To compare the catalytic activities, laboratory equipment is used which corresponds to that in which the catalyst activation is carried out. The reactor used is a 2.5 liter autoclave made of steel and equipped with a stirrer and jacket heater. A manometer and a thermocouple are used to monitor the pressure and the temperature. The input and output quantities of acetylene are measured with an orifice meter.

The reaction parameters are as follows:

| | |
|---|---|
| temperature | 93° C. |
| pressure | 0.5 bars |
| exhaust gas | 40 to 50 ml/min. |

The input substances are as follows:
1000 g of 30% formaldehyde solution
100 g of activated catalyst
1.68 g of 25% aqueous solution of Na-acetate.

The reaction mixture is placed in the reactor and acetylene is introduced with stirring. The reaction is begun at 75° to 80° C. After reaching the temperature of reaction, samples are removed at given times (see table), from which the formaldehyde contents are ascertained. The drop in concentration in $CH_2O$ in the reaction mixture per unit of time is taken as a measure of the catalyst activity. The control test results are summarized in the table below:

| catalysts | formaldehyde in wt % after given hours. | | | | | | | |
|---|---|---|---|---|---|---|---|---|
| | 1 | 2 | 4 | 6 | 9 | 13 | 25 | hrs |
| OLD catalyst | 27 | 25 | 21 | 17 | 12 | 8 | 2 | % |
| FRESH catalyst | 25 | 21 | 15 | 10 | 5 | 2 | 0.1 | % |
| REACTIVATED catalyst | 25 | 21 | 15 | 10 | 6 | 3 | 0.2 | % |

EXAMPLE 2

This example is implemented as is Example 1, however, the average temperature of the catalytic substance is 450° C.

Characteristics of the regenerated catalyst:

| copper content | 28.0% by weight |
|---|---|
| bismuth content | 2.2% by weight |
| carbon content | 0.85% by weight |
| grain size distribution | <10 microns = 25% |
| | <45 microns = 100%. |

Activity:

| formaldehyde content in wt % after given hours | | | | | | | |
|---|---|---|---|---|---|---|---|
| 1 | 2 | 4 | 6 | 9 | 13 | 25 | hours |
| 25 | 21 | 15 | 10 | 6 | 3 | <0.3 | % |

EXAMPLE 3 (CONTROL)

The control example is the same as in Example 1, but the average temperature of the catalytic substance is 800° C.

Characteristics of the regenerated catalyst:

| copper content | 28.9% by weight |
|---|---|
| bismuth content | 1.45% by weight |
| carbon content | 0.31% by weight |
| grain size distribution | <2 microns = 0.5% |
| | <10 microns = 26% |
| | <30 microns = 100%. |

The recovered amount of catalyst contained about 2 to 3% of fairly large sintered clumps (about 1 cm in diameter) that were excluded from the grading analysis.

Activity:

| formaldehyde content in wt % after given hours | | | | | | | |
|---|---|---|---|---|---|---|---|
| 1 | 2 | 4 | 6 | 9 | 13 | 25 | hours |
| 27 | 24 | 19 | 15 | 10 | 6 | 0.5 | % |

We claim:

1. In a process for regenerating suspended heavy metal catalysts comprising a finely divided water insoluble complex cuprous acetylide powder made from a catalyst precursor material containing greater than 20% and less than 35% by weight of copper and 0 to about 3% by weight of bismuth on a magnesium silicate carrier support for the synthesis of butynediol from acetylene and formaldehyde in a reaction mixture thereof, the improvement comprising:
   (a) removing an aqueous catalytic slurry containing said supported heavy metal catalysts from said reaction mixture;
   (b) raising the removed slurry to a temperature of about 200° to 500° C.; and
   (c) maintaining said slurry at said temperature with air being supplied until the carbon content of said supported heavy metal catalysts is reduced to about 0.5 to 3% to form carbon reduced supported catalysts.

2. The process of claim 1, wherein said temperature is about 250°-350° C.

3. The process of claim 2, wherein said carbon content is reduced to less than 1%.

4. The methods of claim 1, wherein said carbon reduced catalyst has a copper content of about 25.3% and a grain size distribution less than 10 microns of about 26%, less than 45 microns about 99.8% and greater than 90 microns about 0.1%.

5. The process of claim 1, wherein step (c) is carried out by revolving said supported heavy metal catalysts to eliminate local overheating.

6. The process of claim 5, wherein said carbon reduced supported catalysts produced by step (c) are reactivated by introducing said catalysts into a formaldehyde solution to form a dispersion, adding acetic acid to said dispersion and treating with acetylene.

* * * * *